(12) United States Patent
Lombardi, III

(10) Patent No.: US 9,534,721 B2
(45) Date of Patent: Jan. 3, 2017

(54) HIGH PRESSURE FLUID CONDUIT CONNECTOR COMPONENTS AND CONNECTOR ASSEMBLY

(71) Applicant: Nordson Corporation, Westlake, OH (US)

(72) Inventor: Francis J. Lombardi, III, Erie, CO (US)

(73) Assignee: NORDSON CORPORATION, Westlake, OH (US)

( * ) Notice: Subject to any disclaimer, the term of this patent is extended or adjusted under 35 U.S.C. 154(b) by 559 days.

(21) Appl. No.: 14/068,703

(22) Filed: Oct. 31, 2013

(65) Prior Publication Data

US 2015/0115598 A1 Apr. 30, 2015

(51) Int. Cl.
*F16L 37/56* (2006.01)
*F16L 37/098* (2006.01)

(52) U.S. Cl.
CPC ............ *F16L 37/56* (2013.01); *F16L 37/0985* (2013.01)

(58) Field of Classification Search
CPC ..................... A61M 39/10; A61M 2039/1027; A61M 39/105; A61M 2039/1044; F16L 37/56; F16L 37/0985
See application file for complete search history.

(56) References Cited

U.S. PATENT DOCUMENTS

| | | | |
|---|---|---|---|
| 3,933,406 A | 1/1976 | Cameron et al. | |
| 4,280,485 A | 7/1981 | Arkans | |
| 4,754,993 A * | 7/1988 | Kraynick | F16L 37/56 285/124.4 |
| 4,804,208 A * | 2/1989 | Dye | F16L 37/56 285/124.4 |
| 4,982,736 A | 1/1991 | Schneider | |
| 5,219,185 A * | 6/1993 | Oddenino | F16L 37/56 285/187 |
| 5,242,425 A | 9/1993 | White et al. | |

(Continued)

FOREIGN PATENT DOCUMENTS

EP 2177808 A1 4/2010

OTHER PUBLICATIONS

Value Plastics, Inc., The SBL Series Quick Connects, SBL001/SG0109, Bar Code 8026-1-1-1/1 (2000) (2 pages).

*Primary Examiner* — David E Bochna
(74) *Attorney, Agent, or Firm* — Baker & Hostetler LLP

(57) ABSTRACT

A high pressure fluid conduit connector includes male and female connector components that releasably snap into engagement with each other to fluidically connect two fluid conduits. The male connector component includes opposing latch arms that extend along a majority of the length of the female connector component when these connector components are engaged with each other. As a result, the engagement of latch catches on the latch arms and latching shoulders on the female connector component occurs near a rear proximal end of the female connector component. This enables a maximum amount of deflection of the latch arms for a given force applied by the user to pivot the latch arms, and the manufacturing of the male and female connector components may be reliably performed by conventional molding processes. Therefore, the fluid conduit connector provides reliable and advantageous operation, especially in high pressure fluid contexts.

27 Claims, 9 Drawing Sheets

(56) References Cited

U.S. PATENT DOCUMENTS

| | | | |
|---|---|---|---|
| 5,246,380 A | 9/1993 | Kodama | |
| 5,478,119 A | 12/1995 | Dye | |
| 5,984,378 A | 11/1999 | Ostrander et al. | |
| 6,062,244 A | 5/2000 | Arkans | |
| 6,402,204 B1 | 6/2002 | Stuart et al. | |
| D508,431 S | 8/2005 | Yoshiguchi | |
| 7,343,931 B2* | 3/2008 | Packham | F16L 37/32 137/614.03 |
| 8,092,409 B2 | 1/2012 | Mros et al. | |
| 8,257,286 B2 | 9/2012 | Meyer et al. | |
| 2005/0184264 A1* | 8/2005 | Tesluk | A61M 39/105 251/148 |
| 2011/0204621 A1 | 8/2011 | Whitaker et al. | |
| 2011/0204622 A1 | 8/2011 | Lewis et al. | |
| 2011/0210541 A1 | 9/2011 | Lewis et al. | |
| 2012/0184931 A1* | 7/2012 | Horn | A61M 39/105 604/319 |

\* cited by examiner

HIGH PRESSURE FLUID CONDUIT CONNECTOR COMPONENTS AND CONNECTOR ASSEMBLY

TECHNICAL FIELD

The present invention generally relates to fluid conduit connectors, and more particularly, to male and female components of a fluid conduit connector assembly having latching and/or locking features to retain the male and female components together regardless of high internal pressures in the fluid conduits.

BACKGROUND

A variety of connect/disconnect coupling assemblies for small flexible tubing applications and other fluid conduit applications are known for use when multiple sections of fluid conduit or tubing need to be connected together. For example, such coupling assemblies are utilized for biomedical applications, convenience handling, beverage dispensing, instrument connections, photochemical handling, etc. The coupling assemblies typically include male and female connector components that releasably couple to each other to retain the multiple sections of fluid conduit or tubing in fluid communication. Typically, these male and female connector components are subject to axial and side loads applied to one or both of the multiple sections of fluid conduit or tubing. In addition, the male and female connector components must remain secured together in a sealed relationship regardless of the internal and external loading applied, and preferably until a user intentionally actuates the disconnection of the male and female connector components from one another.

For many fluid conduit applications, the pressure of the fluid within the fluid conduits is typically in the range of 5 pounds per square inch (psi) to 80 psi. Accordingly, most connector components for the corresponding fluid conduit coupling assemblies include features configured to resist internal loading caused by fluid pressures up to 80 psi. However, some applications require the connection of fluid conduits carrying high pressure fluids that are at much higher pressures than 80 psi. For example, one known application includes fluid conduits that carry pressurized fluid at 1200 psi or more. Many of the conventional connector components are designed for internal loads only up to 80 psi, and these connector components may therefore be insufficient to reliably maintain the coupling of fluid conduits when the internal pressures reach high pressures such as 1200 psi.

Additionally, even if a conventional set of male and female connector components could withstand high internal pressures, the resulting latch geometry formed between the male and female connector components would render the connector components highly difficult to disconnect from one another, even when intended by the user. To this end, a user may need to have an exceedingly high dexterity and/or hand strength to disconnect the conventional connector components in such a setting. This is especially true in circumstances when the male and female connector components are improperly aligned with each other during coupling. In this regard, an improper alignment can cause jamming together of the male and female connector components, and the seals used to withstand internal forces of the high pressure fluids may produce a high amount of friction or stiction that makes it difficult to disconnect the fluid conduit coupling assembly.

For reasons such as these, there is a need for a fluid conduit connector assembly that offers improved coupling security, simplified operation, and decreased manufacturing costs, especially in the context of high pressure fluid conduits.

SUMMARY

In one embodiment, a high pressure fluid conduit connector assembly is configured to releasably couple at least two fluid conduit portions together. The fluid conduit connector assembly includes male and female connector components. The male connector component includes a male connector body portion defining a male distal end and a male proximal end, a first lumen extending from the male distal end, and an elongate first latch arm extending from the male distal end. The first lumen communicates with a first fluid conduit defined by a first elongate bore extending from the male proximal end to the first lumen. The first latch arm defines a first latch catch and a lateral side surface extending between the first latch catch and the male distal end. The lateral side surface includes a finger pad portion. The female connector component includes a female connector body portion defining a female proximal end, a female distal end, and lateral side edges extending along a length between the female proximal and distal ends. The female connector component also includes a first receptacle extending proximally from the female distal end, a second fluid conduit defined by a second elongate bore extending from the first receptacle, and a first latch opening located proximate to one of the lateral side edges. The first latch opening extends from the female distal end to an undercut formed in a portion of the female proximal end, the undercut defining a first latching shoulder proximate the female proximal end. A first access opening in one of the lateral side edges communicates with the first latch opening.

Consequently, the male and female connector components are coupled to each other by inserting the first latch arm into the first latch opening until the first latch catch snaps into engagement with the first latching shoulder. At this point, the male distal end is adjacent or abutting the female distal end, and the first lumen is located inside the first receptacle. Additionally, the lateral side surface of the first latch arm extends along a majority of the length between the female proximal end and the female distal end. The finger pad portion on the first latch arm is positioned so as to be accessible through the first access opening, thereby enabling a user to depress the first latch arm at the finger pad portion to disengage the first latch catch from the first latching shoulder. The male and female connector components are then pulled apart to disconnect these elements.

In one aspect, the female proximal end of the female connector component includes undercuts above and below the first access opening. These undercuts define two first latching shoulders for engaging the first latch catch on opposing sides of the first access opening. Moreover, the first latch opening includes opposing tapered lead-in surfaces above and below the first access opening for guiding the enlarged distal end of the first latch arm to a position where the first latch catch snaps into engagement with the first latching shoulders. The tapered lead-in surfaces may be curved to initially correct for any misalignments of the first latch arm with the first latch opening, and these tapered lead-in surfaces effectively depress or deflect the first latch arm automatically until the latch arm snaps into engagement with the first latching shoulders.

To assist with disconnecting the male and female connector components, the first latch opening further includes an interior surface positioned opposite the first latching shoulders and the tapered lead-in surfaces. This interior surface includes an angled kickout surface portion directly opposite the first latching shoulders so that the enlarged distal end of the first latch arm engages this angled kickout surface portion when the user depresses the finger pad portion to deflect the first latch arm out of engagement with the first latching shoulders. The angled kickout surface portion leverages the inward force applied at the finger pad portion to force the enlarged distal end to slide along the angled kickout surface portion to help break any friction or stiction formed between a seal ring on the first lumen and the first receptacle. Accordingly, the features of the female connector component help accurately guide movement of the male connector component and the first latch arm during actuation by the user.

In some embodiments, the male connector component may include a second lumen and/or a second latch arm, and the female connector component would then include a corresponding second receptacle and/or a second latch opening. The second lumen and second receptacle would communicate with different fluid conduit portions than the first lumen and first receptacle, which means the proper orientation when coupling the male and female connector components is important. To ensure such proper orientation, the male and female connector components also include one or more alignment features used to block or discourage improper coupling of the male and female connector components.

For example, the alignment features may include an elongate post extending from either the male distal end or the female distal end and a corresponding track aperture formed in the other connector component, with each of these elements being aligned along a longitudinal axis that is offset from a central axis through the male and female connector components. In another example, the alignment features include at least one visual indicator in the form of coring or ribs provided along only one side of each of the male and female connector components. The male and female distal ends may include distal end faces with complementary first and second portions having different first and second curvatures that will only abut properly when the male and female connector components are properly aligned. Alternatively or in addition, the contour of the male and female connector components may be curved relative to the central axis such as by defining an asymmetric contour from top to bottom, thereby preventing connection of the male and female connector components except in the proper orientation. In yet another example, the alignment features include a first structure such as an elliptical disc projection extending distally from one of the lateral side edges of the male or female connector component, and a second structure such as an elliptical disc aperture provided in one of the lateral side edges of the other of the male and female connector components. Regardless of how many alignment features are provided, the user will be informed readily of how to connect the male and female connector components properly to assemble the fluid conduit connector assembly.

Advantageously, each of the lumens with corresponding seal rings is provided on a single part, such as the male connector component. This arrangement enables the male connector component to be a reusable piece and the female connector component to be a replaceable or disposable piece that is easily and inexpensively manufactured (e.g., this component is just molded). The lumens may include a tapered portion distal from the seal ring and the receptacles include a tapered lead-in bore section configured to reduce or eliminate frictional contact between the lumens and the receptacles until right before the latch arms snap into engagement with the latching shoulders. Once the latch arms do snap into engagement, the seal ring prevents leakage from the fluid conduits communicating with the lumens and the receptacles.

The male and female connector components are designed to transfer both axial loads and side or radial loads that are applied externally to the fluid conduit connector assembly or internally as a result of pressurized fluids in the fluid conduits. To this end, the elongate post and track aperture, used as one of the alignment features, may also be configured to define a close frictional fit so that side loads are transferred between the male and female connector components at that interface. Any axial loads between the connector components are transferred at the abutments between the male and female distal ends and between the latch catches on the latch arms and the latching shoulders in the female connector component. In view of this, even high amounts of axial and side loads are handled without causing the male and female connector components to unintentionally disconnect.

In some embodiments, the latch arms extend so far into the latch openings of the female connector component that the enlarged distal ends must include central slots to receive central ribs formed in the rear-side openings of the female proximal end. The engagement of these central slots with the central ribs can provide more robustness and interlocking to the connection formed between the male and female connector components. The latch arms may also include a stiffening rib that extends along at least a portion of the first latch arm and projecting inwardly in an opposite direction from the lateral side surface and finger pad portion. The stiffening rib and latch arm may define an I-beam shaped cross section in this portion where the stiffening rib is located. Consequently, the latch arms are encouraged to bend towards the middle and are strengthened to avoid breakage during high force applications.

Another embodiment according to the invention includes a female connector component configured to be coupled to a male connector component. As described above, the female connector component includes a female connector body portion, a first receptacle, a fluid conduit, a first latch opening, and a first access opening. In still another embodiment according to the invention, a male connector component is provided for coupling to a female connector component. This male connector component is as described above and therefore includes a male connector body portion, a first lumen, a first fluid conduit, and an elongate first latch arm.

These and other objects and advantages of the invention will become more readily apparent during the following detailed description taken in conjunction with the drawings herein.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
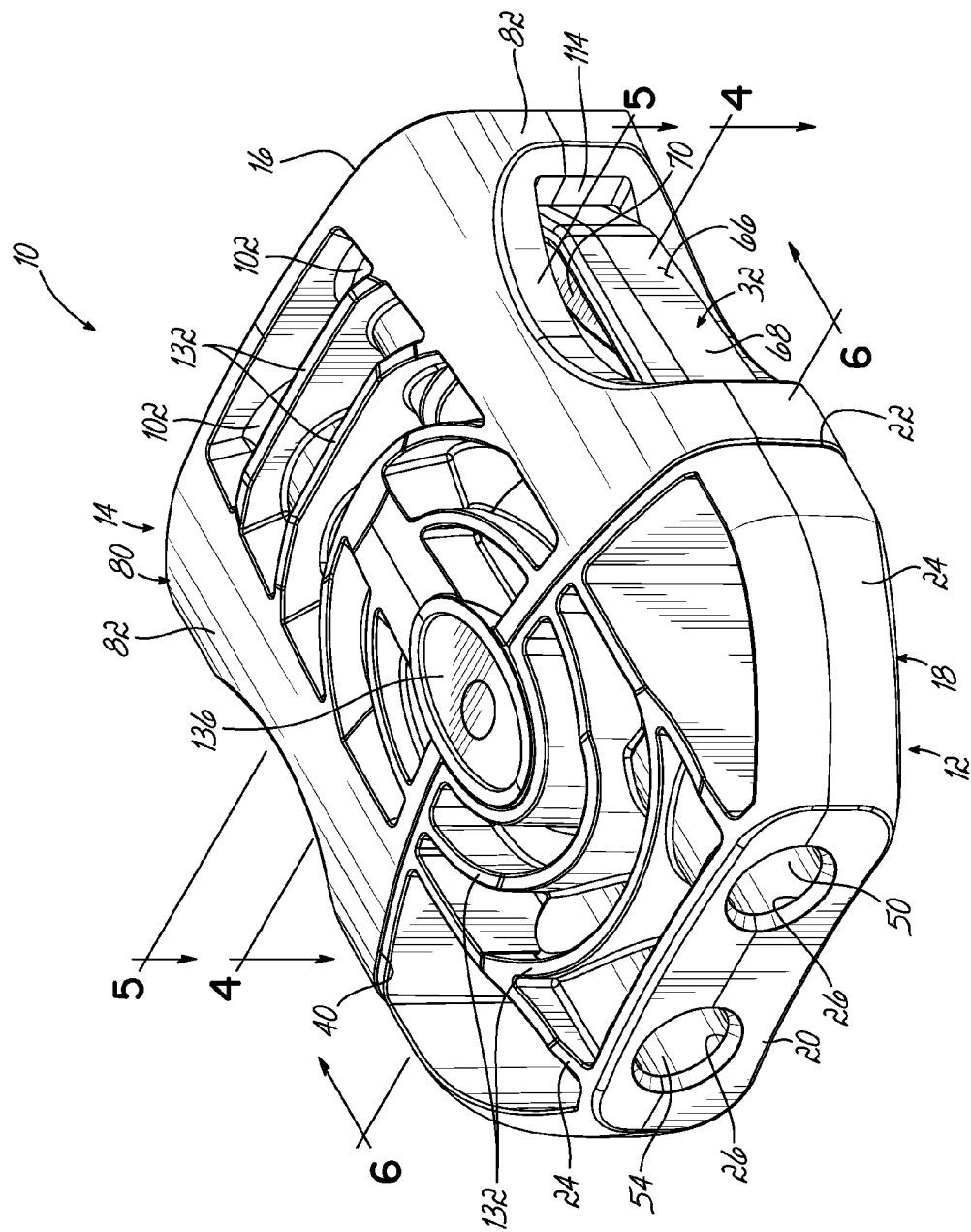
FIG. 1 is a top-side perspective view of a high pressure fluid conduit connector assembly according to a first embodiment of the present invention, with male and female connector components engaged with one another.

Referring to FIGS. 1 through 6, a high pressure fluid conduit connector assembly 10 (also referred to as "fluid conduit connector" 10, throughout) in accordance with one embodiment of the present invention is optimized to retain a male connector component 12 and a female connector component 14 together, regardless of any axial or side loading applied to tubing or flexible fluid conduits that may be coupled to the male and female connector components 12, 14. To this end, the male and female connector components 12, 14 include complementary latching structures that reliably retain the male connector component 12 in various operating conditions, including high pressure in one or more of the fluid conduit lines being connected together by the fluid conduit connector 10. For example, the fluid conduit connector 10 is designed for internal operating pressures of greater than 80 pounds per square inch (e.g., 1200 psi in one particular example). Furthermore, the male and female connector components 12, 14 include multiple interlocking structures configured to both assist with transfer of radial and axial loads between the connector components 12, 14 and ensure proper alignment of the male and female connector components 12, 14 with one another before connection together. Accordingly, the fluid conduit connector 10 provides several advantages compared to known connector assemblies.

Figure 2:
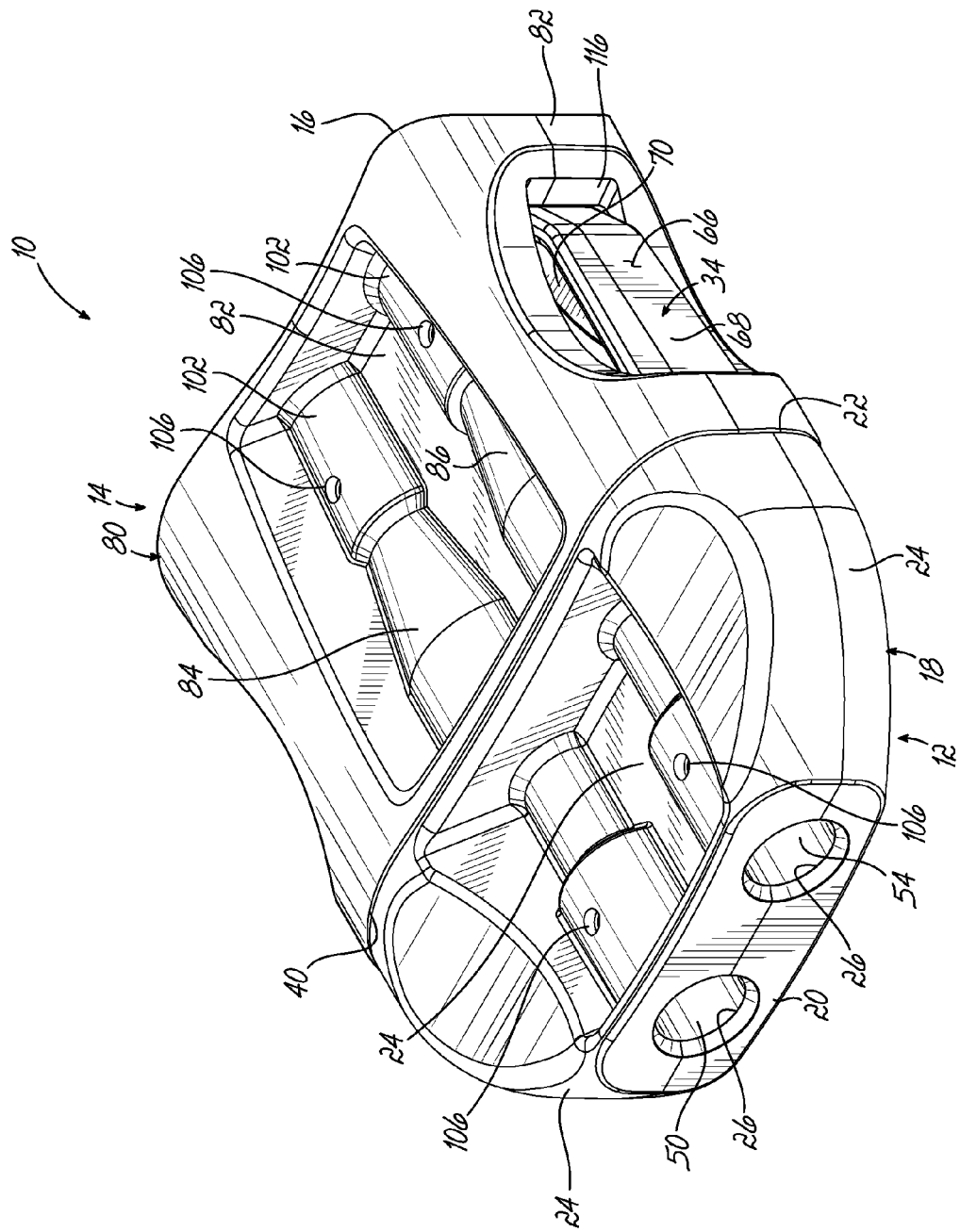
FIG. 2 is a bottom-side perspective view of the fluid conduit connector assembly of FIG. 1.
Figure 3:
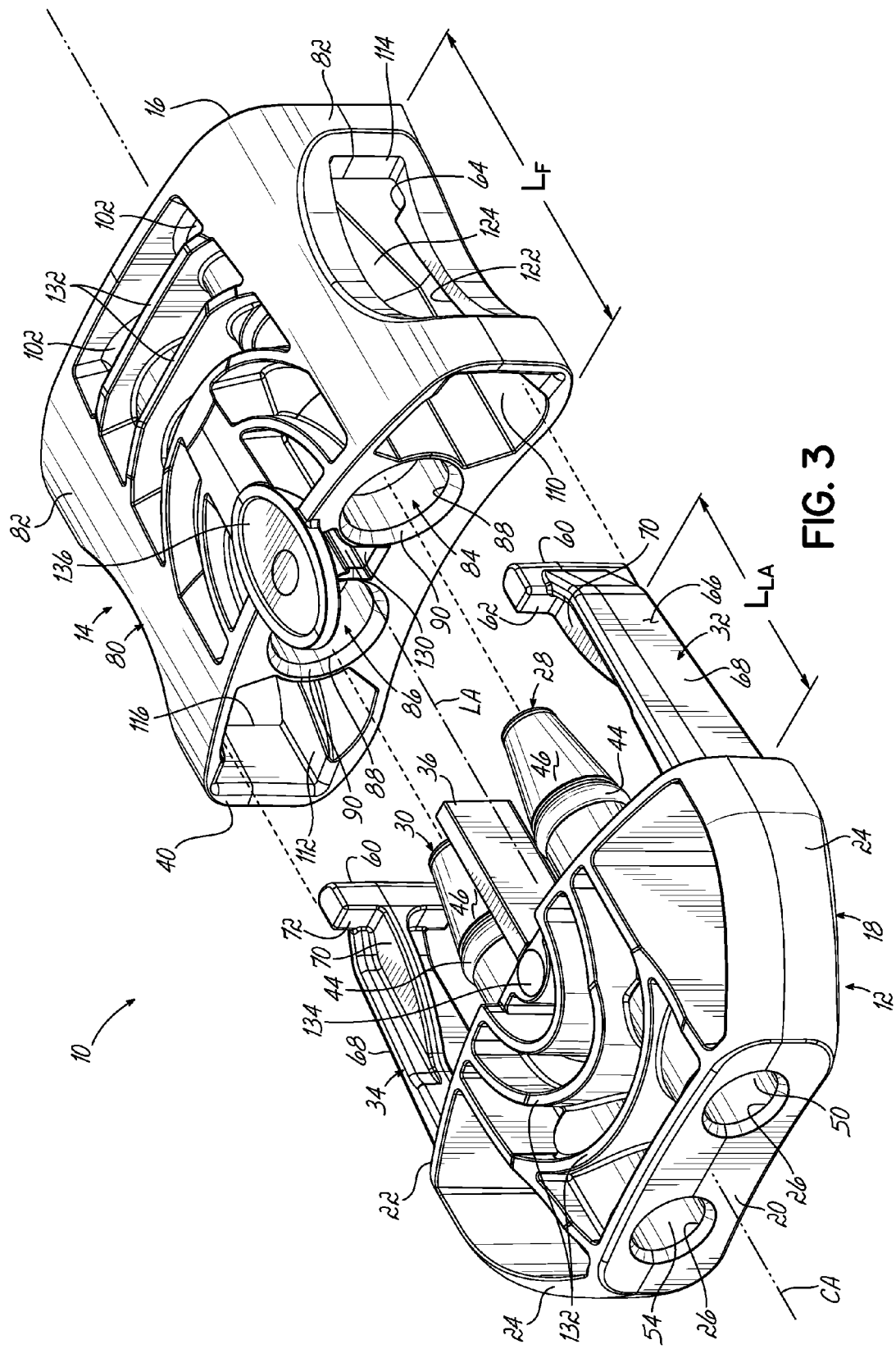
FIG. 3 is a top-side perspective view of the high pressure fluid conduit connector assembly of FIG. 1, where the male and female connector components have been disconnected from one another.

With particular reference to FIGS. 1 through 3, the fluid conduit connector 10 is shown in a coupled together state (FIGS. 1 and 2) as well as a disconnected or exploded apart state (FIG. 3). Each of the male and female connector components 12, 14 are molded as unitary pieces from a plastic material such as polycarbonate, which has sufficient strength to resist the loads applied in high pressure operation. As will be readily understood, it is desirable to design each of the connector components 12, 14 with a minimal number of undercut-like features that are difficult to mold in a standard molding process. Ideally, the connector components 12, 14 are able to be formed in a two-part mold apparatus that can be opened without deforming or breaking molded pieces of the male and female connector components 12, 14. In view of this, the latching structure in the female connector component 14 is formed as an "undercut" that is open towards a female proximal end 16 and therefore forms a portion of the female proximal end 16. This advantageously enables the latching of the male and female connector components 12, 14 to occur proximate to the female proximal end 16, as described in further detail below.

With continued reference to FIGS. 1 through 3, the male connector component 12 is illustrated in further detail. The male connector component 12 includes a male connector body portion 18 defined by a male proximal end 20 and a male distal end 22 with a plurality of lateral side edges 24 extending between the male proximal and distal ends 20, 22. The male proximal end 20 is configured to face away from the female connector component 14 during assembly and includes a pair of conduit openings 26 that are configured to receive and be connected to corresponding fluid conduit portions (not shown), as well understood in the field of fluid conduit connectors. These tubular fluid conduit portions may be held in position within the generally cylindrical conduit openings 26 by friction-enhancing barbs or other similar known structures provided on the free ends of the fluid conduit portions (in another example, locking fasteners may be used to retain the fluid conduit portions in the conduit openings 26 as described in further detail below). The male distal end 22 is configured to face towards the female connector component 14 and abut the female connector component 14 during assembly. In this regard, the male connector component 12 further includes various structures extending and projecting distally from the male distal end 22 to interact with complementary structures formed in the female connector component 14. In this exemplary embodiment, these structures include a first lumen 28, a second lumen 30, elongate first and second latch arms 32, 34, and an elongate alignment post 36. Each of these elements is described in further detail below, but it will be understood that more or fewer lumens and/or more or fewer latch arms may be used in other embodiments of the fluid conduit connector 10 without departing from the scope of the invention.

It will be appreciated that the use of the terms "distal and proximal" throughout this specification and the claims is intended to provide a frame of reference for each element of these male and female connector components 12, 14. More specifically, "distal" refers to a direction towards the other connector component 12, 14 when the male and female connector components 12, 14 are secured to each other, and this direction is also away from the portion of flexible tubing or conduit that is coupled to the male or female connector component 12, 14. Likewise, "proximal" refers to a direction away from the other connector component 12, 14 and towards the connected portion of flexible tubing or conduit. Furthermore, "axial" is used to refer to lengths and movements along or parallel to a longitudinal axis through the male and female connector component 12, 14, while "radial" is used to refer to a direction perpendicular to the axial direction. The terms "above" and "below" are also used to refer to specific radial directions as shown in the Figures, although it will be understood that these labels are not intended to limit how the fluid conduit connector 10 is used and oriented during operation.

The male distal end 22 defines a generally planar or slightly curved solid surface from which each of the lumens 28, 30 and latch arms 32, 34 projects. As described below, the male distal end 22 is shaped or contoured to be complementary with a female distal end 40 on the female connector component 14 when these male and female distal ends 22, 40 are brought into adjacent alignment or abutment during coupling of the fluid conduit connector 10. To this end, the curvature of the male distal end 22 (when present) matches the curvature of the corresponding female distal end 40. As described in examples below, the curvatures may be asymmetric in one or more directions to act as an alignment feature for properly orienting and connecting the male and female connector components 12, 14. Consequently, the male distal end 22 is able to transfer axial loads to and from the male connector component 12 as a result of this interfacial abutment with the female distal end 40 as shown in FIGS. 1 and 2.

The first and second lumens 28, 30 are hollow members that extend from the male connector body portion 18 to provide fluid communication with the female connector component 14 after assembly of the fluid conduit connector 10. Each of the first and second lumens 28, 30 are identical in the exemplary embodiment shown (and so only one is described in detail below), although it will be understood that the first lumen 28 may define a different shape and size than the second lumen 30 in other embodiments. Moreover, the male connector component 12 may include only one lumen or more than two lumens in other embodiments (the number of lumens may vary regardless of the number of latch arms included), depending on the needs of the end user. As shown in FIG. 3, the first lumen 28 includes an external seal groove 42 configured to receive a seal ring 44 such as a sealing O-ring. The seal ring 44 is separately formed from a resilient or elastomeric material and is added to the first lumen 28 after the initial molding of the male connector component 12. The second lumen 30 includes an identical seal groove 42 and seal ring 44. When the first and second lumens 28, 30 are inserted into the female connector component 14, the seal rings 44 engage with the female connector component 14 to prevent leakage from the interface between the first and second lumens 28, 30 and corresponding structures in the female connector component 14 described below.

Advantageously, only the male connector component 12 includes the lumens 28, 30 and the seal rings 44, as this enables the other piece (e.g., the female connector component 14) to be a unitary molded piece that is easily replaceable and used as a disposable unit, if necessary. The male connector component 12 in such embodiments is designed to be a reusable piece, thereby limiting the manufacturing time and expense needed because the lumens 28, 30 and seal rings 44 do not need to be assembled each time a fluid conduit connector 10 is used. It will be understood that the seal rings 44 could instead be provided only on the female connector component to render that piece reusable (and the male connector component would therefore be a unitary piece that could be replaceable or disposable) in other embodiments in accordance with the invention.

Each of the first and second lumens 28, 30 also includes a tapered portion 46 extending distally from the seal groove 42. This tapered portion 46 is configured to guide the lumens 28, 30 into the female connector component 14 and reduce frictional engagement between the seal rings 44 and the female connector component 14 before reaching a final desired position. The tapered portion 46 also reduces the amount of deformation that the seal ring 44 has to undergo during assembly of the seal ring 44 onto the seal groove 42 of the lumens 28, 30.

As briefly noted above, the first lumen 28 is hollow and therefore defines a portion of a first fluid conduit 48 (not shown in detail until FIG. 4A) extending through the male connector component 12. The first fluid conduit 48 is also at least partially defined by a first elongate bore 50 that extends from the male proximal end 20 to the first lumen 28. The first fluid conduit 48 and the first elongate bore 50 define a generally cylindrical and continuous diametrical cross-section along the length of the male connector component 12, except at the conduit opening 26 at the male proximal end 20, which is slightly larger than the remainder of the first fluid conduit 48. As a result, the conduit opening 26 is sized to receive a tubular fluid conduit (not shown) so that this tubular fluid conduit may be retained in communication with the first fluid conduit 48 and the first lumen 28. In a similar fashion, the second lumen 30 defines a portion of an additional fluid conduit 52 extending through the male connector component 12, the additional fluid conduit 52 including an additional elongate bore 54 extending between the other conduit opening 26 and the second lumen 30. In operation, the first fluid conduit 48 and first lumen 28 may receive a first fluid at a first pressure, and the additional fluid conduit 52 and second lumen 30 may receive a second fluid having a different composition and/or pressure than the first fluid. Accordingly, the correct orientation and connection of these lumens 28, 30 carrying distinct fluids to corresponding structure in the female connector component 14 needs to be assured with the use of one or more alignment features described in further detail below for the fluid conduit connector 10. For example, the elongate alignment post 36 projecting from the male distal end 22 may be offset from a longitudinal center of the male connector component 12 in one type of alignment feature, although others are also provided in the exemplary embodiment as well.

The first and second latch arms 32, 34 extend from the male distal end 22 along opposing lateral side edges 24. To this end, the first and second lumens 28, 30 are positioned so as to be in between the first and second latch arms 32, 34. This positioning of the latch arms 32, 34 enables ready access to a user to actuate connection and disconnection of the male and female connector components 12, 14 as described in connection with FIGS. 4A through 5C below. The first latch arm 32 includes an enlarged distal end 60 that defines a first latch catch 62. More particularly, the first latch catch 62 is a generally planar surface that extends generally perpendicular to the remainder of the first latch arm 32 and is configured to snap into engagement with a corresponding first latching shoulder 64 (not shown in detail until FIG. 4A) formed in the female connector component 14. The remainder of the first latch arm 32 includes a lateral side surface 66 that extends between the enlarged distal end 60 and the male distal end 22 of the male connector component 12. This lateral side surface 66 faces outwardly away from the first and second lumens 28, 30 and includes a finger pad portion 68 defined along at least a portion of its length. The finger pad portion 68 is configured to be pushed by a user to disengage the latched engagement of the first latch catch 62 and the first latching shoulder 64 when the fluid conduit connector 10 is in use.

On an opposite side of the first latch arm 32 from the lateral side surface 66 (e.g., facing inwardly towards the first and second lumens 28, 30), the first latch arm 32 also includes a stiffening rib 70 extending at least along a portion of the length between the enlarged distal end 60 and the male distal end 22. In the example shown in the illustrated embodiment, the stiffening rib 70 extends along approximately half of the first latch arm 32 (specifically, the distal-most half adjacent to the enlarged distal end 60). The stiffening rib 70 shown in FIG. 3 is a planar piece of material that is generally centered on the first latch arm 32 and is oriented generally perpendicular to both the remainder of the first latch arm 32 and the surfaces defining the first latch catch 62 at the enlarged distal end 60. Although this stiffening rib 70 provides a generally T-shaped cross section for the first latch arm 32 along a portion of the length thereof, it will be understood that the stiffening rib 70 may define other shapes and sizes in other embodiments without departing from the scope of the invention. The stiffening rib 70 reinforces the first latch arm 32 precisely at the point where the first latch arm 32 is designed to flex or bend, thereby reducing the risk of latch arm breakage under excessive flexing or abusive conditions. In this regard, the stiffening rib 70 effectively forces the first latch arm 32 to bend towards a middle portion thereof initially and then distributes the flexing forces applied to the first latch arm 32 over the entire length of the first latch arm 32. The stiffening rib 70 improves longevity and robustness of the first latch arm 32, which is especially useful in embodiments where the male connector component 12 is designed to be a reusable piece with a long service life.

The second latch arm 34 is configured to be identical to the first latch arm 32 in this embodiment (and the same reference numbers have been applied to many of the same elements described above), but the second latch arm 34 is rotated 180 degrees in orientation so that the lateral side surface 66 on the second latch arm 34 continues to face outwardly away from the first and second lumens 28, 30. Likewise, the stiffening rib 70 of the second latch arm 34 extends inwardly away from the lateral side surface 66 towards the first and second lumens 28, 30. The enlarged distal end 60 of the second latch arm 34 defines a second latch catch 72, which is a generally planar surface that extends generally perpendicular to the remainder of the second latch arm 34 and is configured to snap into engagement with a corresponding second latching shoulder 74 formed in the female connector component 14. In view of the identical construction of the first and second latch arms 32, 34, the first and second latch catches 62, 72 are configured to snap into engagement with the first and second latching shoulders 64, 74 at the same time when connecting the male and female connector components 12, 14. Of course, it will be appreciated that one or both of the latch arms 32, 34 may be modified in profile and/or shape in alternative embodiments. Furthermore, the male connector component 12 may include only one latch arm or more than two latch arms in other embodiments consistent with the invention.

With reference to FIGS. 1 through 4A, additional details of the female connector component 14 are shown in further detail. The female connector component 14 includes a female connector body portion 80 that includes the aforementioned female proximal end 16 and female distal end 40. The female connector body portion 80 is also defined by a plurality of lateral side edges 82 that extend along a length $L_F$ of the female connector component 14 between the female proximal and distal ends 16, 40. Instead of including a plurality of projecting structures that extend away from the female connector body portion 80 like the male connector component 12 includes, the female connector component 14 includes a plurality of internal features and spaces that extend inwardly from one or more of the female proximal end 16, the female distal end 40 and/or the lateral side edges 82 to provide room for the projecting structures of the male connector component 12 when the fluid conduit connector 10 is fully assembled. These internal features are described in further detail below.

Figure 4A:
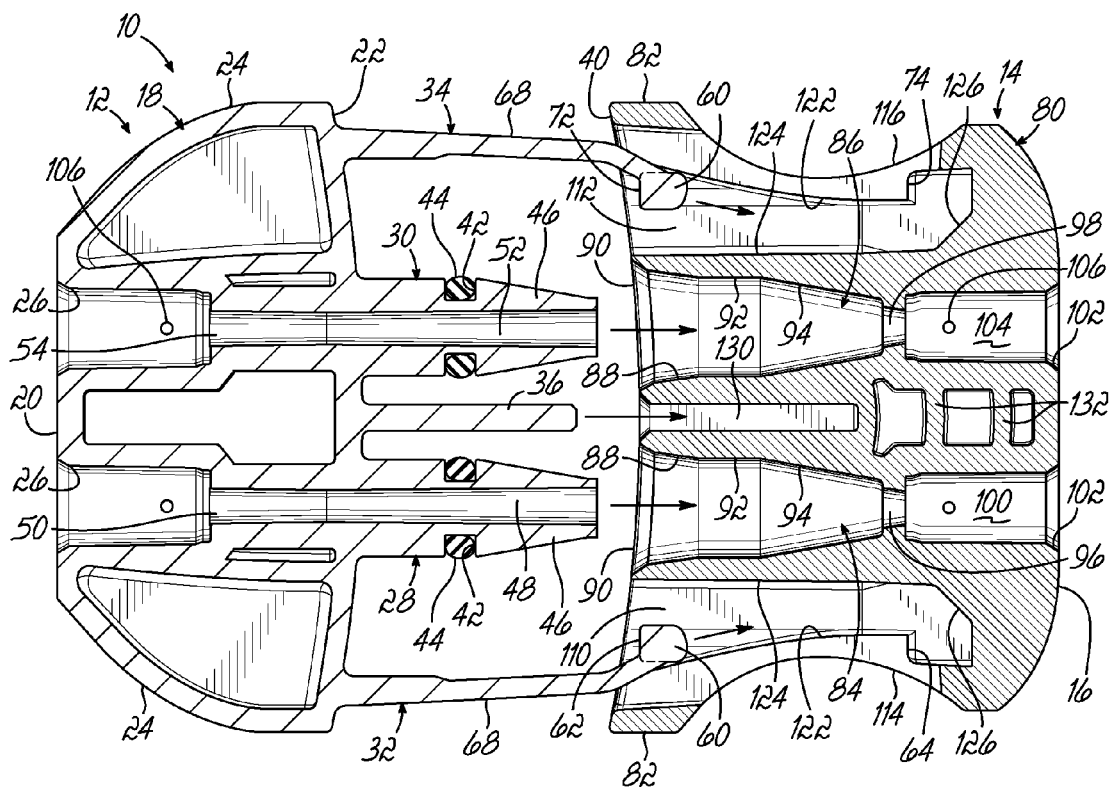
FIG. 4A is a cross-sectional top view of the high pressure fluid conduit connector assembly of FIG. 1, sectioned along line 4-4 in FIG. 1 to reveal internal latch and bore components of the male and female connector components beginning to interact with each other during a first part of connecting the components together.

As shown most clearly in FIGS. 3 and 4A, the female connector component 14 includes first and second receptacles 84, 86 extending proximally from the female distal end 40 and configured to receive the corresponding first and second lumens 28, 30. Each of the first and second receptacles 84, 86 are sized and shaped to receive the respective lumens 28, 30 with the seal rings 44 sealingly engaging the receptacles 84, 86 after coupling the male and female connector components 12, 14 together. Additionally, using the first receptacle 84 as an example of the identical construction for both receptacles 84, 86, and this first receptacle 84 includes a tapered lead-in bore section 88 extending inwardly into the female connector body portion 80 from a receptacle opening 90 formed in the female distal end 40. The tapered lead-in bore section 88 is larger in diameter than a largest part of the first lumen 28 and therefore reduces or eliminates frictional engagement of the first lumen 28 and the seal ring 44 with the first receptacle 84 during most of the insertion of the first lumen 28 into the first receptacle 84. Beyond the tapered lead-in bore section 88, the first receptacle 84 includes a cylindrical bore section 92 configured to sealingly engage the seal ring 44 and a tapered bore tip end 94 configured to receive the tapered portion 46 of the first lumen 28. As will be readily understood, the tapered lead-in bore section 88 of the first receptacle 84 also assists with guiding the first lumen 28 into correct positioning and alignment with the first receptacle 84 during initial insertion of the first lumen 28 into the female connector body portion 80.

The second receptacle 86 includes each of the same features, including the receptacle opening 90, the tapered lead-in bore section 88, the cylindrical bore section 92, and the tapered bore tip end 94. It will be understood that the particular shape and size of the first and second receptacles 84, 86 may be modified in other embodiments to match varying sizes and shapes for the lumens 28, 30. Moreover, only one receptacle or more than two receptacles would be provided in the female connector component 14 to match a different number of lumens when provided in the male connector component 12.

Similar to each of the first and second lumens 28, 30, the first and second receptacles 84, 86 define a portion of a second fluid conduit 96 and an additional fluid conduit 98, respectively, extending through the female connector component 14. The second fluid conduit 96 is also at least partially defined by a second elongate bore 100 that extends from the female proximal end 16 to the first receptacle 84. The second elongate bore 100 includes a conduit opening 102 at the female proximal end 16, which is slightly larger than the remainder of the second elongate bore 100. As a result, the conduit opening 102 is sized to receive a tubular fluid conduit (not shown) so that this tubular fluid conduit may be retained in communication with the second fluid conduit 96 and the first receptacle 84. When fully assembled, the fluid conduit connector 10 therefore provides a first fluid path providing fluid communication from the tubular fluid conduit coupled to the conduit opening 26 in the male connector component 12, through each of the first fluid conduit 48, first lumen 28, first receptacle 84, and second fluid conduit 96 to the tubular fluid conduit coupled to the conduit opening 102 in the female connector component 14. In this regard, the sealed connection of the first lumen 28 into the first receptacle 84 is configured to prevent leakage when the tubular fluid conduits connected to the male and female connector components 12, 14 are put into fluid communication by assembling the fluid conduit connector 10, even at high operating pressures within the tubular fluid conduits such as 1200 psi or greater.

Similarly, the additional fluid conduit 98 includes an additional elongate bore 104 extending between another conduit opening 102 at the female proximal end 16 and the second receptacle 86. Consequently, a second fluid path is defined in the fluid conduit connector 10 that provides communication from the tubular fluid conduit coupled to the other conduit opening 26 in the male connector component 12, through each of the additional fluid conduit 52, second lumen 30, second receptacle 86, and the other additional fluid conduit 98 to the tubular fluid conduit coupled to the other conduit opening 102 in the female connector component 14. As alluded to above, the composition or pressure of the fluid in this second fluid path may be distinct from the fluid in the first fluid path in some operations. Advantageously, the male and female connector components 12, 14 are designed to remain reliably latched together even when internal loading caused by distinct pressures in the first and second fluid paths causes a transmission of axial and/or radial side loads between the male and female connector components 12, 14.

As shown most clearly in FIGS. 2 and 4A, each of the two conduit openings 26 in the male connector component 12 and each of the two conduit openings 102 in the female connector component 14 defines a generally cylindrical shape configured to receive the free ends of tubular fluid conduits inserted into the male and female connector components 12, 14. These tubular fluid conduits may be held in position by friction-enhancing barbs or other similar known structures provided on the free ends of the tubular fluid conduits. Alternatively, each of the conduit openings 26, 102 also communicates with a respective aperture 106 extending through one of the lateral side edges 24, 82. Each of the apertures 106 is configured to receive a locking fastener (not shown) or some other similar element used to engage with the free ends of the tubular fluid conduits and hold these tubular fluid conduits in position within the male and female connector components 12, 14. Such locking fasteners in the apertures 106 are particularly useful when the fluid conduit connector 10 is used with tubular fluid conduits carrying high pressure fluids such as at 1200 psi or greater. It will be understood that other methods of securing and retaining the free ends of the tubular fluid conduits in the conduit openings 26, 102 may be used in alternative embodiments consistent with the scope of the invention.

The female connector component 14 also includes first and second latch openings 110, 112 configured to receive the first and second latch arms 32, 34 when the male and female connector components 12, 14 are coupled together. Each of the first and second latch openings 110, 112 extends from the female distal end 40 to the female proximal end 16 along opposing lateral side edges 82 of the female connector component 14. Between the female distal end 40 and the female proximal end 16, the first and second latch openings 110, 112 each communicate with corresponding first and second access openings 114, 116 formed in the opposing lateral side edges 82. These first and second access openings 114, 116 provide access to a user to depress the finger pad portions 68 of the first and second latch arms 32, 34 when the first and second latch arms 32, 34 are engaged with the first and second latching shoulders 64, 74 in the female connector component 14. This access to the latch arms 32, 34 is most clearly shown in the fully assembled position of the fluid conduit connector 10 shown in FIGS. 1 and 2.

The first access opening 114 extends along a majority of the length $L_F$ of the female connector component 14, but terminates short of the female distal end 40 and the female proximal end 16. More particularly, the first access opening 114 is positioned to divide the first latching shoulder 64 formed by an undercut in the female proximal end 16 into two first latching shoulders 64a, 64b located above and below (in the context of FIGS. 1 through 3) the first access opening 114. However, as the enlarged distal end 60 of the first latch arm 32 projects outwardly to define the first latch catch 62 on both upper and lower sides of the lateral side surface 66, the first latch catch 62 snaps into engagement with each of these two first latching shoulders 64a, 64b. The simultaneous engagement of the first latch catch 62 with two first latching shoulders 64a, 64b enhances the reliability of the connection formed between the first latch arm 32 and the female connector component 14. The second access opening 116 is identical to the first access opening 114 and therefore also splits the second latching shoulder 74 into two second latching shoulders 74a, 74b located above and below the second access opening 116. Just like the first latch arm 32, the second latch arm 34 simultaneously snaps into engagement at the second latch catch 72 with both of the two second latching shoulders 74a, 74b. To this end, the male connector component 12 and the latch arms 32, 34 provide four distinct points of engaged contact used to transfer forces between the components and for reliably maintaining the fluid conduit connector 10 in the assembled position.

Advantageously, the undercuts defining the first latching shoulder 64 and the second latching shoulder 74 in a portion of the female proximal end 16 are formed proximate to the remainder of the female proximal end 16. Although the female connector component 14 is still sized to substantially enclose each of the enlarged distal ends 60 of the first and second latch arms 32, 34 when the male and female connector components 12, 14 are coupled to one another, the first and second latch catches 62, 72 are located substantially at the female proximal end 16. In this regard, the lateral side surfaces 66 of each of the first and second latch arms 32, 34, which extends between the respective latch catches 62, 72 and the male distal end 22, also extends along a majority of the length $L_F$ of the female connector component 14 as defined between the female proximal and distal ends 16, 40 in the fully assembled position. As a result, the length $L_{LA}$ of a pivoting portion of the latch arms 32, 34 (e.g., the lateral side surfaces 66) defined between the latch catches 62, 72 and the male distal end 22 is maximized, thereby maximizing the amount of lateral deflection achieved when bending or pivoting the first and second latch arms 32, 34. This maximized length also increases the effective size of the lateral side surfaces 66 and the finger pad portions 68, which may provide better leverage for a user to deflect the latch arms 32, 34 easily when it is desired to disconnect the male and female connector components 12, 14. However, the four points of contact between the first and second latch catches 62, 72 and the first and second latching shoulders 64, 74 avoid unintentional disconnection of the snap engagement between the male and female connector components 12, 14 until the user actuates this disconnection by depressing the finger pad portions 68 and deflecting the latch arms 32, 34.

In addition to the benefits described above of the current fluid conduit connector 10 compared to conventional connector assemblies (which typically include latch catches more closely to the female distal end of female connector components rather than proximate to the female proximal end), the positioning of the first and second latching shoulders 64, 74 as undercuts proximate to the female proximal end 16 provides additional benefits. To this end, the manufacturing of the female connector component 14 is rendered possible by a simple molding process because the "undercuts" formed in the female proximal end 16 communicate outwardly through rear-side openings 118 (FIG. 5A) defined in the female proximal end 16 because the latch openings 110, 112 extend all the way from the female distal end 40 to the female proximal end 16. In addition, with the undercuts being molded within the interior of the latch openings 110, 112, the outer contours of the female connector body portion 80 remain smooth and no sharp edges are presented that could catch on a user's clothing or other equipment. This smooth contour along the lateral side edges 82 of the female connector component 14 provides a desirable appearance and tactile feel for a user of the fluid conduit connector 10. Consequently, the placement and construction of the latch arms 32, 34 and the female connector component 14 provides several advantages improving fluid conduit connector assemblies 10, especially when used with high pressure fluids.

As discussed above, the first access opening 114 divides the first latching shoulder 64 into two such shoulders 64*a*, 64*b*. In addition, the outermost surface of the first latch opening 110 formed by the female connector body portion 80 above and below the first access opening 114 is also broken into two opposing tapered lead-in surfaces 122 extending from the female distal end 40 to the first latching shoulder 64 (e.g., latching shoulders 64*a*, 64*b*). The tapered lead-in surfaces 122 define a gently curved profile that flattens out and becomes substantially planar and perpendicular to the first latching shoulder 64 adjacent the intersection between the tapered lead-in surfaces 122 and the first latching shoulder 64. Accordingly, the enlarged distal end 60 of the first latch arm 32, which is also rounded to enhance the sliding contact between these elements, is guided to slide along the tapered lead-in surfaces and automatically be deflected inwardly as the male connector component 12 is pushed into engagement with the female connector component 14. Once the enlarged distal end 60 slides beyond the end of the tapered lead-in surfaces 122, the first latch catch 62 snaps outwardly into engagement with the first latching shoulder 64, as a result of the first latch arm 32 resiliently deflecting back to a substantially non-deflected position. Consequently, the tapered lead-in surfaces 122 accurately position and guide the first latch arm 32 during coupling of the male and female connector components 12, 14. It will be understood that the particular curvature and profile of the tapered lead-in surfaces 122 may be modified in other embodiments.

The second access opening 116 also divides the second latching shoulder 74 into two such shoulders 74*a*, 74*b*, and similar tapered lead-in surfaces 122 are also provided above and below the second access opening 116. Just as described above, the tapered lead-in surfaces 122 in the second latch opening 112 engage the enlarged distal end 60 of the second latch arm 34 and guide that distal end 60 during movement of the second latch arm 34 into the second latch opening 112. To this end, the tapered lead-in surfaces 122 also automatically deflect or depress the second latch arm 34 inwardly until the enlarged distal end 60 reaches the second latching shoulders 74, at which point the second latch arm 34 snaps resiliently outwardly such that the second latch catch 72 engages with the second latching shoulders 74. It will be understood that this latching action is configured to happen simultaneously with the first latch catch 62 engaging with the first latching shoulders 64.

Each of the first and second latch openings 110, 112 also includes an interior surface 124 opposite the corresponding access openings 114, 116 and the tapered lead-in surfaces 122. The interior surface 124 is substantially flat and planar (in an axial or longitudinal direction) except at an angled kickout surface portion 126 located directly opposite the first and second latching shoulders 64, 74. The angled kickout surface portions 126 in the first and second latch openings 110, 112 project outwardly towards the first and second latching shoulders 64, 74 and towards the lateral side edges 82 of the female connector body portion 80. For example, the angled kickout surface portions 126 may be angled at about 45 degrees from the remainder of the interior surfaces 124.

As a result of this positioning, the angled kickout surface portions 126 are configured to engage the enlarged distal ends 60 of the first and second latch arms 32, 34 when those latch arms 32, 34 are deflected inwardly by a user to disconnect the first and second latch catches 62, 72 from the first and second latching shoulders 64, 74. It is known that a high amount of static friction or stiction may occur between the seal rings 44 on the first and second lumens 28, 30 and the first and second receptacles 84, 86 after full assembly of the fluid conduit connector 10, and the angled kickout surface portions 126 advantageously help break this stiction. In this regard, the deflected or depressed latch arms 32, 34 engage at the enlarged distal ends 60 against the angled kickout surface portions 126 and further inward deflection will force the enlarged distal ends 60 to slide outwardly along those angled kickout surface portions 126, thereby allowing the inward pressing on the finger pad portions 68 to be leveraged fully to break the stiction between seal rings 44 and receptacles 84, 86. It will be understood that the interior surfaces 124 and the angled kickout surface portions 126 may be modified in contour, positioning, and angling in other embodiments depending on the preferences of the end user.

Consequently, the features and contours defined within each of the first and second latch openings 110, 112 enable easy and intuitive use of the fluid conduit connector 10. To couple the male and female connector components 12, 14 together, the latch arms 32, 34 just need to be inserted and pressed into the latch openings 110, 112 so that the enlarged distal ends 60 ride along the tapered lead-in surfaces 122 until the latch catches 62, 72 snap into engagement with the latching shoulders 64, 74. To disconnect the male and female connector components 12, 14 following use, a user must simply press on the finger pad portions 68 of the lateral side surfaces 66 on each of the latch arms 32, 34 and the angled kickout surface portion 126 (as well as possibly the curved tapered lead-in surfaces 122) guides the latch arms 32, 34 back out of the latch openings 110, 112. As such, the snap engagement of the male and female connector components 12, 14 is reliable yet easy to disconnect when that is intended by a user.

In embodiments of the fluid conduit connector 10 with multiple lumens 28, 30 and multiple receptacles 84, 86 such as the exemplary embodiment shown in FIGS. 1 through 6, one or more alignment features may be provided to either force or encourage a user to properly align the correct lumens 28, 30 with the correct receptacles 84, 86 during assembly of the fluid conduit connector 10. A first example of such an alignment feature includes the elongate alignment post 36 that projects distally from the male distal end 22 of the male connector body portion 18 and a corresponding track aperture 130 extending in a proximal direction from the female distal end 40 into the interior of the female connector body portion 80. The track aperture 130 and the alignment post 36 are each offset from a central axis CA of the male and female connector components 12, 14 such that the track aperture 130 and the alignment post 36 define a longitudinal axis LA (FIG. 3) that is offset from the central axis CA. As a result of this offset, the alignment post 36 would run into a solid portion of the female distal end 40 if the male connector component 12 were flipped over from the orientation shown in FIG. 3 and pushed towards the female connector component 14. The only way that the male and female connector components 12, 14 can be pushed together to the fully assembled state of FIGS. 1 and 2 is if the alignment post 36 is properly aligned with the track aperture 130, and this prevents engagement of the male and female connector components 12, 14 in a reversed or improper orientation (e.g., where the first lumen 28 would be inserted into the second receptacle 86 and the second lumen 30 would be inserted into the first receptacle 84). Other structural features of the male and female connector components 12, 14 may be provided offset from the central axis CA in other embodiments, such as having the first and second latch arms 32, 34 each be offset in similar directions from the central axis CA so as to prevent connection of the male and female connector components 12, 14 in an improper orientation, for example.

The alignment post 36 and the track aperture 130 also provide additional advantageous benefits for the fluid conduit connector 10. To this end, the track aperture 130 is dimensioned to closely receive the alignment post 36, perhaps even in a slightly frictional or interference-type fit. The tighter engagement of the alignment post 36 and the track aperture 130 compared to the lumens 28, 30 in the receptacles 84, 86 enables the transfer of side or radial loading to be transmitted between the male and female connector components 12, 14 at the interface between the alignment post 36 and the track aperture 130. Regardless of whether such a side load occurs based on differential internal pressures in the first and second lumens 28, 30 or based on external forces from outside the fluid conduit connector 10, the loads are not applied and transferred at the location of the flow paths and the location of the seal rings 44. Similarly, axial loads between the male and female connector components 12, 14 are transferred at the abutments between the latch catches 62, 72 and latching shoulders 64, 74 and/or at the abutment between the male and female distal ends 22, 40 of the corresponding male and female connector body portions 18, 80, which is also away from the lumen-receptacle engagement. Consequently, all types of forces and loads that may be applied to either of the male and female connector components 12, 14 will be reliably transferred to the other component without tending to disengage the coupling of these elements.

In order to save on materials used to mold the male and female connector components 12, 14, the lateral side edges 24, 82 of the male and female connector body portions 18, 80 may include coring out of material outside of the locations of elements such as the receptacles 84, 86 and the various fluid conduits 48, 52, 96, 98. In order to serve as another example of an alignment feature, this coring may define a plurality of ribs 132 along only one of the lateral side edges 24, 82 (e.g., the top sides visible in FIG. 1) and no ribs 132 along an opposite one of the lateral side edges 24, 82 (e.g., the bottom sides visible in FIG. 2). By coring the male and female connector body portions 18, 80 to include ribs 132 only along one side, a visual and a tactile indicator for a user is provided which confirms when the male and female connector components 12, 14 are properly aligned for assembly, as in FIG. 3. If the male connector component 12 were flipped over from the orientation shown in FIG. 3, a user would readily see or feel that the contours provided along the top and bottom sides defined by the lateral side edges 24, 82 do not match. Therefore, the user will recognize that the male connector component 12 would need to be reoriented so that the lateral side edges 24, 82 including coring with ribs 132 on each of the male and female connector body portions 18, 80 were brought into adjacent relation with one another when assembling the fluid conduit connector 10.

It will be understood that the molding of the male and female connector components 12, 14 is also designed to provide smooth contours around the entire periphery of the male and female connector body portions 18, 80. These smooth contours can be seen in the fully assembled state of the fluid conduit connector 10 shown in FIGS. 1 and 2. Furthermore, the specific smooth curvature provided along the first and second access openings 114, 116 naturally encourages a user to grasp the fluid conduit connector 10 at those locations where the finger pad portions 68 may be accessed. Consequently, even a user unfamiliar with the particular design of this fluid conduit connector 10 will be encouraged by the contours of the male and female connector components 12, 14 to grip the fluid conduit connector 10 in desired locations. As such, the male and female connector body portions 18, 80 encourage proper use of the fluid conduit connector 10 while also providing a superior tactile feel for the hands of a user.

Additional types of alignment features are also possible. The male distal end 22 and the female distal end 40 are configured to come into abutting relation in the fully assembled position of the fluid conduit connector 10, so these surfaces may be formed with asymmetric contours around the central axis CA to prevent or discourage connection of the male and female connector components 12, 14 in the wrong orientation. This type of alignment feature is further described with reference to FIGS. 7 and 8 below. The male and female connector body portions 18, 80 may also include complementary first and second structures 134, 136 along the lateral side edges 24, 82 that are configured to engage with one another only when the male and female connector components 12, 14 are in the proper aligned orientation with each other. As shown in FIGS. 1 through 3, an example of the first structure 134 is an elliptical disc aperture in the top side of the male connector body portion 18 that is configured to be aligned with the exemplary second structure 136, which is an elliptical disc projecting extending distally from the female connector body portion 80. As will be readily understood, these first and second structures 134, 136 would not come into engagement/alignment if the male connector component 12 was flipped over or otherwise improperly oriented relative to the female connector component 14. Therefore, the provision of one or more of these alignment features avoids connection of the male and female connector components 12, 14 in an improper orientation.

With reference to FIGS. 4A through 6, the process for coupling and disconnecting the male and female connector components 12, 14 is shown in steps. In FIGS. 4A and 5A, the male connector component 12 has been properly aligned with the female connector component 14 and the two elements are beginning to be brought together. In this initial engagement state, the enlarged distal ends 60 of the first and second latch arms 32, 34 are inserted into the first and second latch openings 110, 112 and are engaged with the tapered lead-in surfaces 122. From this position, the first and second latch arms 32, 34 are guided automatically to move in the path indicated by the arrows in FIGS. 4A and 5A as the male and female connector components 12, 14 are pushed further towards one another.

Figure 4B:
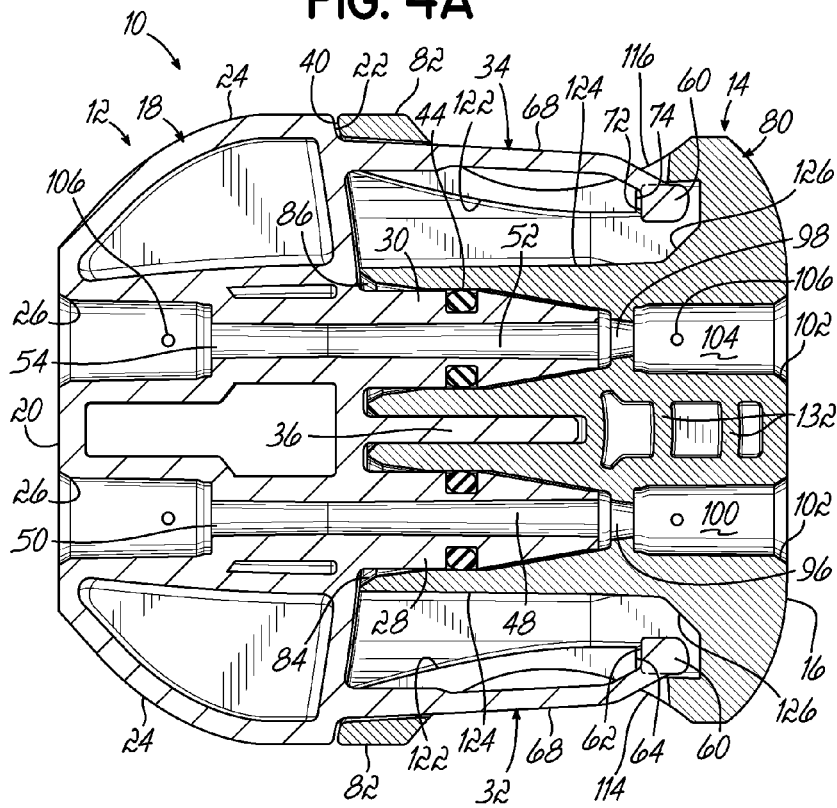
FIG. 4B is a cross-sectional top view of the high pressure fluid conduit connector assembly of FIG. 4A, sectioned along line 4-4 in FIG. 1 to reveal internal latch and bore components of the male and female connector components in a fully coupled position of these elements.
Figure 5A:
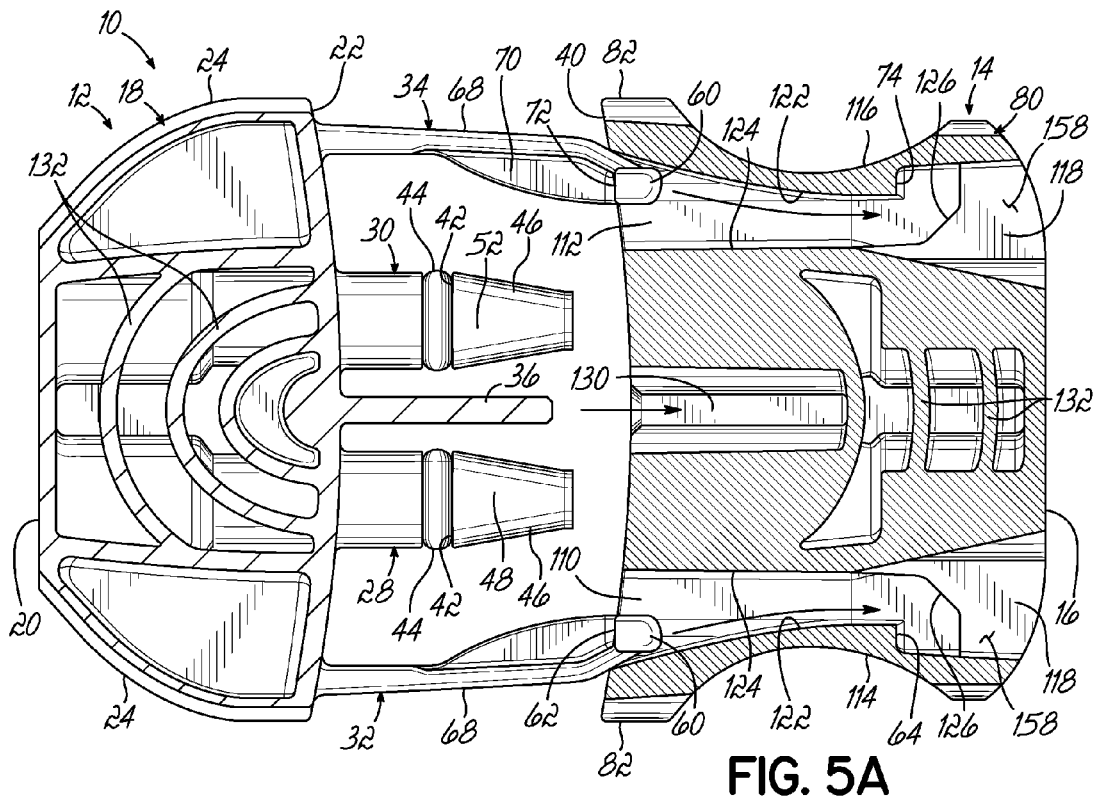
FIG. 5A is a cross-sectional top view of the high pressure fluid conduit connector assembly of FIG. 4A, sectioned along line 5-5 in FIG. 1 to reveal internal latch and bore components of the male and female connector components beginning to interact with each other during the first part of connecting the components together.
Figure 5B:
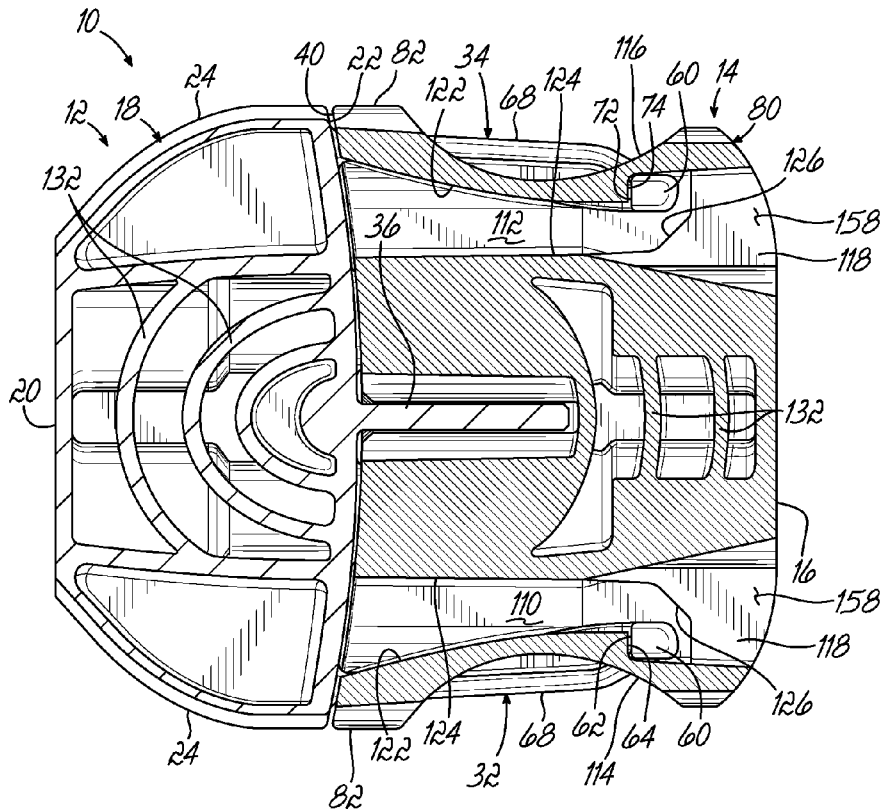
FIG. 5B is a cross-sectional top view of the high pressure fluid conduit connector assembly of FIG. 4B, sectioned along line 5-5 in FIG. 1 to reveal internal latch and bore components of the male and female connector components in the fully coupled position of these elements.

Turning to FIGS. 4B and 5B, the male and female connector components 12, 14 have been fully assembled into snap engagement with one another. In this position, the lateral side surfaces 66 of the latch arms 32, 34 extend along a majority of the length $L_F$ of the female connector body portion 80 and the latch catches 62, 72 are engaged with the corresponding latching shoulders 64, 74. In addition, the finger pad portions 68 on the lateral side surfaces 66 move into communication with the first and second access openings 114, 116 formed in the lateral side edges 82 of the female connector component 14. Also in this position, the first and second lumens 28, 30 have been brought into engagement with the corresponding first and second receptacles 84, 86. The seal rings 44 prevent any fluid leakage from the conduits now brought into communication by the fluid conduit connector 10. This fully assembled state of the fluid conduit connector 10 is also shown in the cross-sectional view of FIG. 6 to illustrate the relative positioning of elements of the male and female connector components 12, 14. The fluid conduit connector 10 will reliably stay in this fully assembled state until a user manually depresses the latch arms 32, 34 at the finger pad portions 68.

Figure 5C:
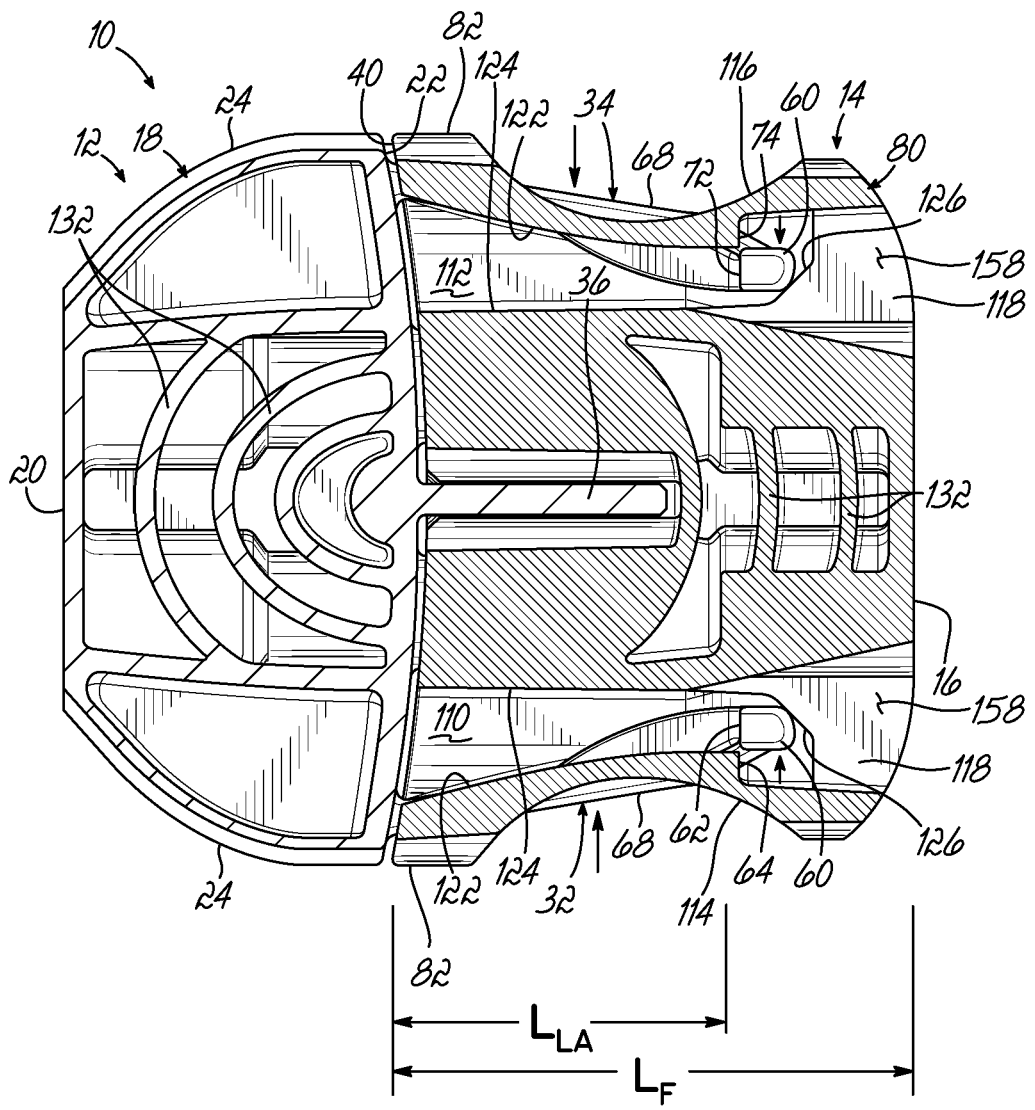
FIG. 5C is a cross-sectional top view of the high pressure fluid conduit connector assembly of FIG. 5B, sectioned along line 5-5 in FIG. 1 to reveal internal latch and bore components of the male and female connector components during a first part of disconnecting the male and female connector components from each other.
Figure 6:
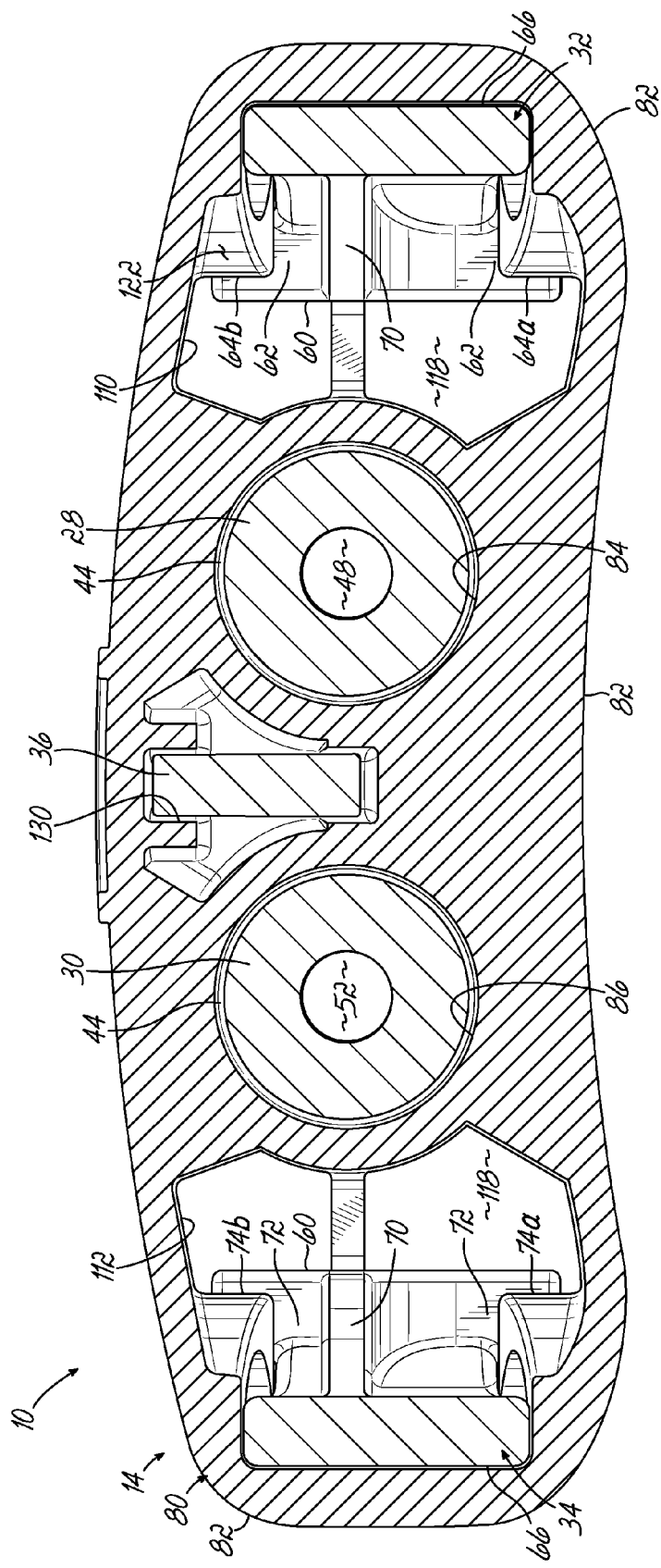
FIG. 6 is a cross-sectional end view of the high pressure fluid conduit connector assembly of FIG. 1, showing internal features of the male and female connector components following movement of the male connector component into the fully coupled position relative to the female connector component.

This disconnection process includes the step shown in FIG. 5C. As shown in that Figure, the user has depressed the finger pad portions 68 through the first and second access openings 114, 116 in order to deflect the latch arms 32, 34 as shown by the arrows. This deflection also pulls the latch catches 62, 72 away from engagement with the corresponding latching shoulders 64, 74. Almost immediately after this disconnection, the enlarged distal ends 60 of both latch arms 32, 34 come into abutment with the angled kickout surface portions 126 formed in the interior surfaces 124 of the latch openings 110, 112. This abutment causes further inward forces applied by the user to force the latch arms 32, 34 to slide along the kickout surface portions 126 and out of the latch openings 110, 112. As described above, the user's force to deflect the latch arms 32, 34 is leveraged fully to break any stiction formed between the seal rings 44 on the lumens 28, 30 and the receptacles 84, 86. Thus, the male connector component 12 can continue to be withdrawn from the female connector component 14 back to the position shown in FIGS. 4A and 5A. As evidenced by these figures showing the connection and disconnection process, the assembly and disassembly of the fluid conduit connector 10 is quick and simple, yet also reliable to avoid unintended disconnections of the fluid conduits, even at high operating pressures.

Figure 7:
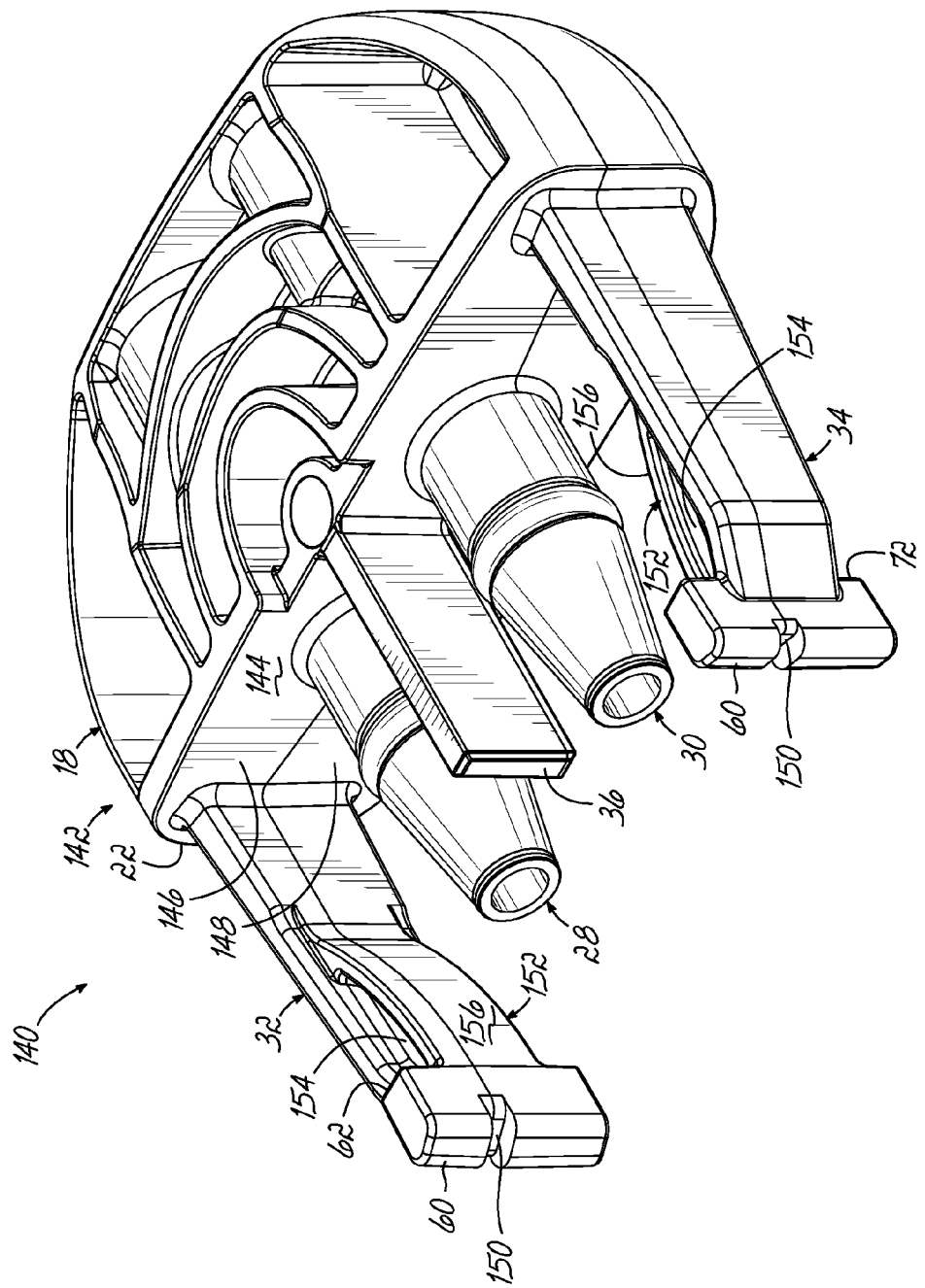
FIG. 7 is a perspective view of a male connector component used with an alternative embodiment of the high pressure fluid conduit connector assembly, including modifications to the latch arms and the distal end of the male connector body portion.
Figure 8:
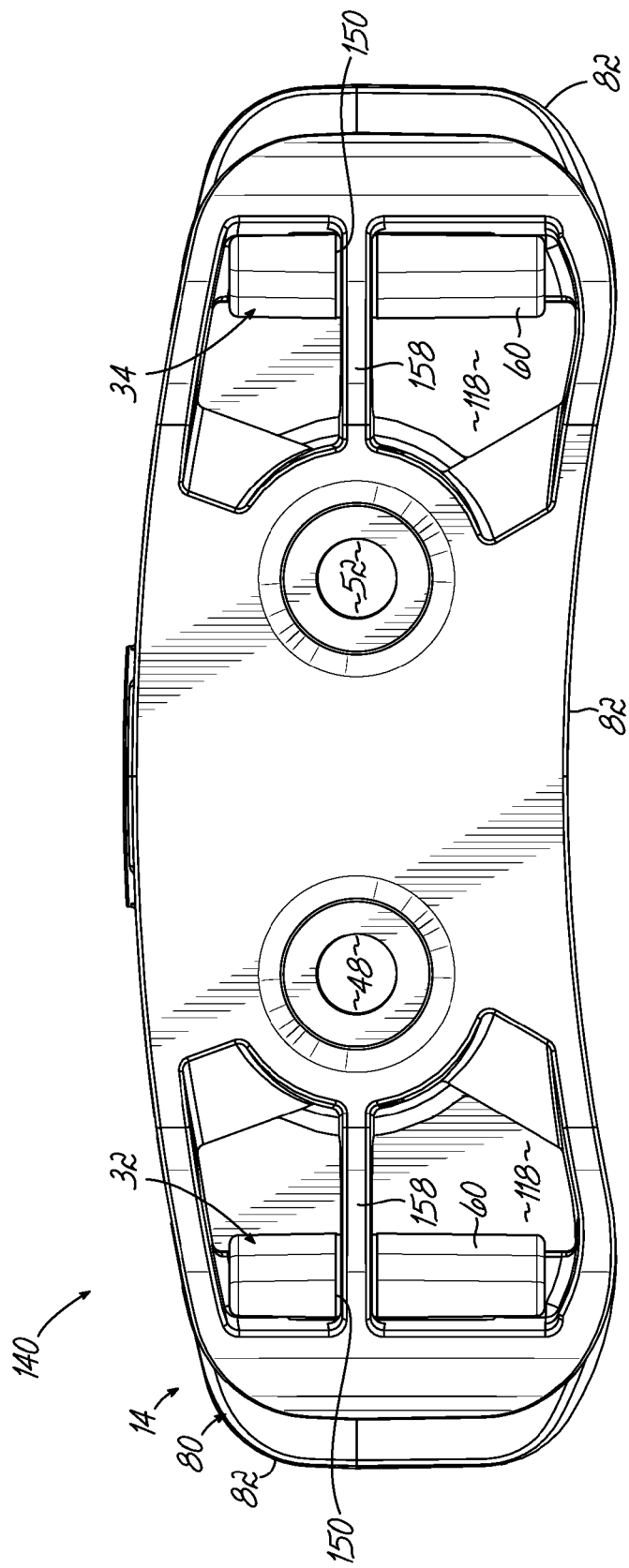
FIG. 8 is a rear-side view of the alternative embodiment of the high pressure fluid conduit connecter, with the male connector component inserted fully into latched engagement with the female connector component.

With reference to FIGS. 7 and 8, an alternative embodiment of the fluid conduit connector 140 is shown in detail. Many of the features of this alternative embodiment are substantially or completely identical to those described above in the first exemplary embodiment, and these elements are not described in further detail below. Additionally, these elements have been provided with identical reference numbers where appropriate. The only changes for this alternative embodiment that are highlighted below are modifications to the male connector component 142 at the latch arms 32, 34, and changes to the male distal end 22 of the male connector body portion 18.

Beginning with the male distal end 22 shown most clearly in FIG. 7, this male distal end 22 includes another type of alignment feature which was initially alluded to above. More particularly, the male distal end 22 defines an asymmetrical male end face 144 that is configured to abut a complementary asymmetrical female end face (not shown) formed on the female distal end 40 of the female connector component 14. For example, the asymmetrical male end face 144 in FIG. 7 includes first and second portions, such as an upper end face portion 146 and a lower end face portion 148. The upper end face portion 146 is shaped to define a first curvature which is distinct from a second curvature defined by the lower end face portion 148. In one example, the upper end face portion 146 is substantially planar with only a small amount of curvature, if any, and the lower end face portion 148 is curved similarly to the first exemplary embodiment. It will be understood that the asymmetrical female end face would have an outwardly curved portion with the second curvature and a generally planar portion with the first curvature. As a result, if the male and female connector components 142, 14 were engaged in an improper or reversed orientation, the different curvatures of the male distal end 22 and the female distal end 40 would prevent these elements from "nesting" or coming into close abutment, and would likely therefore also prevent these elements from latching into engagement at the latch catches 62, 72 and latching shoulders 64, 74. Just like the other alignment features described above, the asymmetrical male end face 144 provides guidance for a user to know how to properly connect and disconnect the fluid conduit connector 140. It will be understood that the particular portions and types of profile or curvatures (both along the distal ends 22, 40 and along the length or central axis of the connector components 142, 14) may be modified in other embodiments without departing from the scope of the invention.

The latch arms 32, 34 are also modified as shown in FIG. 7. To this end, each of the enlarged distal ends 60 of the first and second latch arms 32, 34 includes a central slot 150 formed on an opposite side from the latch catches 62, 72. In this regard, the central slot 150 faces towards the female proximal end 16 as the male and female connector components 142, 14 of the fluid conduit connector 140 are assembled. The latch arms 32, 34 also include a modification to the stiffening rib, specifically an I-beam shaped stiffening rib 152 is formed along the interior surfaces of the latch arms 32, 34. The stiffening rib 152 includes a projecting portion 154 which extends generally perpendicular from opposite the lateral side surface 66 (which is also included in the stiffening rib 70 of the previous embodiment) and a transverse portion 156 extending generally perpendicular to the projecting portion 154 and also spaced from the lateral side surface 66 along most of the length of the stiffening rib 152. The I-beam type design that is produced for the portion of the latch arms 32, 34 where the stiffening rib 152 is located provides maximum support and strength for the amount of material needed to mold the latch arms 32, 34. However, the deflection of the latch arms 32, 34 and the operation relative to the features of the female connector component 14 remain the same as described above for the first embodiment.

With reference to FIG. 8, the engagement of the central slots 150 in the enlarged distal ends 60 of the latch arms 32, 34 with corresponding central ribs 158 provided in the female connector component 14 is shown. To this end, the latch arms 32, 34 are effectively extended further in length from the male distal end 22 than in the previous embodiment, which would cause the enlarged distal ends 60 to run into the central ribs 158 that extend across the rear-side openings 118 at the female proximal end 16 as shown. To accommodate for this, the central slots 150 are added so that the central ribs 158 in the female connector component 14 seat into the central slots 150 of the enlarged distal ends 60 of the latch arms 32, 34 when the latch arms 32, 34 are snapped into engagement with the latching shoulders 64, 74 on the female connector component 14. This additional engagement between the central slots 150 and the central ribs 158 helps the latch arms 32, 34 resist any forces or torques applied by internal or external forces, even those internal forces associated with high pressure fluids (e.g., 1200 psi or greater) in the fluid conduits. Accordingly, the latch arms 32, 34 of this embodiment of the male connector component 142 and the fluid conduit connector 140 provide further reliability in remaining fully assembled until the user actuates the disconnection of the connector components 142, 14.

Consequently, the high pressure fluid conduit connectors 10, 140 of both described embodiments are capable of reliably retaining fluid conduits together, even when those fluid conduits carry highly pressurized fluids. In addition, the male and female connector components 12, 14 are easy and intuitive to actuate during the coupling and disconnection steps for a user because of the smooth contours and the profiles guiding movement of the latch arms 32, 34 to and from engagement with the latching shoulders 64, 74. When a user does desire to disconnect the male and female connector components 12, 14, the large size of the finger pad portions 68 and the large pivoting length of the lateral side surfaces 66 provides maximum deflection away from the latching shoulders 64, 74 with the force applied by the user, which improves the operability of the fluid conduit connectors 10, 140. As such, the fluid conduit connectors 10, 140 provide numerous benefits and advantages compared to conventional connectors, especially in the context of highly pressurized fluids.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A high pressure fluid conduit connector assembly configured to releasably couple at least two fluid conduit portions, the connector assembly comprising:
    a male connector component including a male connector body portion defining a male proximal end and a male distal end, a first lumen extending distally from said male distal end, a first fluid conduit defined by a first elongate bore extending from said male proximal end of said male connector body portion to said first lumen, and an elongate first latch arm extending distally from said male distal end, said first latch arm being deflectable, said first latch arm including an enlarged distal end defining a first latch catch and a lateral side surface extending between said first latch catch and said male distal end, said lateral side surface including a finger pad portion; and
    a female connector component including a female connector body portion defining a female proximal end, a female distal end configured to face said male distal end, and lateral side edges extending along a length between said female proximal and distal ends, said female connector component also including a first receptacle extending proximally from said female distal end, a second fluid conduit defined by a second elongate bore extending from said first receptacle, and a first latch opening located proximate to one of said lateral side edges and extending from said female distal end to an undercut formed in a portion of said female proximal end, said undercut defining a first latching shoulder proximate said female proximal end, said first latch opening communicating with a first access opening in one of said lateral side edges, wherein said first access opening extends between said undercut and said female distal end,
    said male and female connector components being coupled to each other by inserting said first latch arm into said first latch opening to deflect said first latch arm until said first latch catch snaps into engagement with said first latching shoulder, at which point said male distal end is adjacent to said female distal end, said first lumen is located inside said first receptacle, said lateral side surface of said first latch arm extends along a majority of the length between said female proximal and distal ends, and said finger pad portion of said first latch arm is positioned at said first access opening so that a user can depress said first latch arm at said finger pad portion to disengage said first latch catch from said first latching shoulder.

2. The high pressure fluid conduit connector assembly of claim 1, wherein said female proximal end includes undercuts above and below said first access opening, thereby defining two first latching shoulders for engaging said first latch catch on opposing sides of said first access opening when said first latch arm is inserted into said first latch opening.

3. The high pressure fluid conduit connector assembly of claim 2, wherein said first latch opening includes opposing tapered lead-in surfaces above and below said first access opening for guiding said enlarged distal end of said first latch arm to a position where said first latch catch snaps into engagement with said first latching shoulders.

4. The high pressure fluid conduit connector assembly of claim 3, wherein said first latch opening includes an interior surface positioned opposite said first latching shoulders and said tapered lead-in surfaces, said interior surface including an angled kickout surface portion located opposite said first latching shoulders and configured to engage said enlarged distal end of said first latch arm after depression of said first latch arm to unlatch said first latch catch from said first latching shoulders, thereby guiding said first latch arm out of said first latch opening and breaking any stiction formed between said first lumen and said first receptacle.

5. The high pressure fluid conduit connector assembly of claim 1, wherein said male connector component further includes a second lumen extending distally from said male distal end and a second latch arm extending distally from said male distal end to an enlarged distal end defining a second latch catch, with said first and second lumens located between said first and second latch arms, and wherein said female connector component further includes a second receptacle extending proximally from said female distal end to receive said second lumen and a second latch opening located proximate to one of said lateral side edges and extending from said female distal end to an undercut formed in a portion of said female proximal end to define a second latching shoulder configured to snap into engagement with said second latch catch.

6. The high pressure fluid conduit connector assembly of claim 5, wherein said second lumen and said second receptacle communicate with additional fluid conduits in said male and female connector components, said additional fluid conduits configured to carry a different fluid than said first and second fluid conduits communicating with said first lumen and said first receptacle.

7. The high pressure fluid conduit connector assembly of claim 5, further comprising:

an alignment feature provided on each of said male and female connector components, said alignment features preventing latching engagement of said male and female connector components unless said first lumen is aligned with said first receptacle and said second lumen is aligned with said second receptacle.

8. The high pressure fluid conduit connector assembly of claim 7, wherein said alignment features further comprise:

an elongate post extending distally from said male distal end of said male connector component; and a track aperture in said female connector component that is sized to closely receive said elongate post when said male and female connector components are coupled together, wherein said elongate post and said track aperture each define a longitudinal axis that is offset from a central axis through said male and female connector components.

9. The high pressure fluid conduit connector assembly of claim 7, wherein said male connector component includes lateral side edges extending between said male proximal end and said male distal end, and said alignment features further comprise:

at least one visual indicator in the form of coring or ribs formed in only one of said lateral side edges of said female connector component and formed in only one of said lateral side edges of said male connector component, wherein said ones of said lateral side edges of said male and female connector components are configured to be located adjacent each other when said male and female connector components are properly aligned and coupled together.

10. The high pressure fluid conduit connector assembly of claim 7, wherein said alignment features further comprise:

an asymmetrical male distal end face at said male distal end of said male connector component that includes a first portion defining a first curvature and a second portion defining a second curvature; and an asymmetrical female distal end face at said female distal end of said female connector component that includes a first portion defining the first curvature and a second portion defining the second curvature, wherein the first and second curvatures are different such that said asymmetrical male and female distal end faces nest with one another only when said male and female connector components are properly aligned and coupled together.

11. The high pressure fluid conduit connector assembly of claim 7, wherein said male connector component includes lateral side edges extending between said male proximal end and said male distal end, and said alignment features further comprise:

a first structure projecting distally from one of said lateral side edges of one of said male and female connector components, said first structure including an elliptical disc projection; and a second structure recessed into one of said lateral side edges of the other of said male and female connector components, said second structure including an elliptical disc aperture configured to receive said elliptical disc projection when said male and female connector components are properly aligned and coupled together.

12. The high pressure fluid conduit connector assembly of claim 5, wherein said first and second lumens include seal rings, and wherein said male connector component includes all lumens with seal rings that are included with the connector assembly such that said male connector component defines a reusable piece configured to engage a plurality of replaceable female connector components.

13. The high pressure fluid conduit connector assembly of claim 5, further comprising:

an elongate alignment post extending distally from said male distal end of said male connector component; and a track aperture in said female connector component that is sized to closely receive said elongate post when said male and female connector components are coupled together, wherein said elongate post and said track aperture assist with transmitting side or lateral loads between said male and female connector components.

14. The high pressure fluid conduit connector assembly of claim 5, wherein said second latch arm includes a lateral side surface with a finger pad portion, and wherein said male connector body portion and said female connector body portion are each contoured along external surfaces in a complementary manner so as to encourage a user to manually grasp the connector assembly along said finger pad portions of said first and second latch arms.

15. The high pressure fluid conduit connector assembly of claim 1, wherein said first lumen includes a seal ring and a tapered portion positioned distally from said seal ring, and wherein said first receptacle further includes a tapered lead-in bore section configured to reduce frictional engagement between said first receptacle and said seal ring on said first lumen during insertion or removal of said first lumen relative to said first receptacle.

16. The high pressure fluid conduit connector assembly of claim 1, wherein said female connector component includes a central rib projecting into said first latch opening from said female proximal end, and said enlarged distal end of said first latch arm includes a central slot sized to receive said central rib of said female connector component to further interlock said first latch arm with said female connector component when said male and female connector components are coupled together.

17. The high pressure fluid conduit connector assembly of claim 1, wherein said first latch arm also includes a stiffening rib projecting inwardly and opposite said lateral side surface, said stiffening rib extending along at least a portion of said first latch arm between said enlarged distal end and said male distal end of said male connector body portion.

18. The high pressure fluid conduit connector assembly of claim 17, wherein said stiffening rib and said first latch arm collectively define an I-beam shaped cross section at said portion of said latch arm.

19. The high pressure fluid conduit connector assembly of claim 1, wherein said enlarged distal end and said first latch catch are substantially enclosed within said female connector body portion when said male and female connector components are coupled to each other.

20. A female connector component configured to be coupled to a male connector component to form a high pressure fluid conduit connector assembly, the male connector component having a male connector body portion, a first lumen, and a first latch arm with a first latch catch, the female connector component comprising:
 a female connector body portion defining a female proximal end, a female distal end configured to face toward the male connector component, and lateral side edges extending along a length between said female proximal and distal ends;
 a first receptacle extending proximally from said female distal end and sized to receive the first lumen of the male connector component;
 a fluid conduit defined by an elongate bore extending from said first receptacle;
 a first latch opening located proximate one of said lateral side edges and extending from said female distal end to an undercut formed in a portion of said female proximal end, said undercut defining a first latching shoulder proximate said female proximal end; and
 a first access opening in one of said lateral side edges communicating with said first latch opening,
 wherein said first latching shoulder is positioned in said female connector body portion such that the first latch arm of the male connector component extends along a majority of a length between said female distal end and said female proximal end when the male and female connector components are snapped into engagement at the first latch catch and said first latching shoulder, and the first latch arm is accessible through said first access opening for a user to disengage the first latch catch from said first latching shoulder,
 wherein said female proximal end includes undercuts above and below said first access opening, thereby defining two first latching shoulders for engaging the first latch catch on opposing sides of said first access opening when the first latch arm is inserted into said first latch opening, and
 wherein said first latch opening includes opposing tapered lead in surfaces above and below said first access opening for guiding the first latch arm to a position where the first latch catch snaps into engagement with said first latching shoulders.

21. The female connector component of claim 20, wherein said first latch opening includes an interior surface positioned opposite said first latching shoulders and said tapered lead in surfaces, said interior surface including an angled kickout surface portion located opposite said first latching shoulders and configured to engage the first latch arm after depression of the first latch arm to unlatch the first latch catch from said first latching shoulders, thereby guiding the first latch arm out of said first latch opening and breaking any stiction formed between the first lumen and said first receptacle.

22. The female connector component of claim 20, wherein the male connector component further includes a second lumen and a second latch arm defining a second latch catch, with the first and second lumens located between the first and second latch arms, and the female connector component further comprises:
 a second receptacle extending proximally from said female distal end to receive the second lumen; and
 a second latch opening located proximate one of said lateral side edges and extending from said female distal end to an undercut formed in a portion of said female proximal end to define a second latching shoulder configured to snap into engagement with the second latch catch.

23. The female connector component of claim 22, further comprising:
 an alignment feature configured to interact with another alignment feature on the male connector component to thereby prevent latching engagement of the male and female connector components unless the first lumen is aligned with said first receptacle and the second lumen is aligned with said second receptacle, wherein said alignment feature includes at least one of:
 an elongate post or aperture positioned offset from a central axis through the male and female connector components;
 a visual indicator in the form of coring or ribs formed in only one of said lateral side edges; and
 an elliptical disc projection or elliptical disc aperture.

24. The female connector component of claim 20, wherein the first lumen includes a seal ring and a tapered portion positioned distally from the seal ring, and wherein said first receptacle further includes a tapered lead-in bore section configured to reduce frictional engagement between said first receptacle and the seal ring on the first lumen during insertion or removal of the first lumen relative to said first receptacle.

25. A male connector component configured to be coupled to a female connector component to form a high pressure fluid conduit connector assembly, the female connector component having a female connector body portion with female proximal and distal ends, a first receptacle, and a first latch opening with an undercut defining a first latching shoulder proximate the female proximal end and communicating with a first access opening, the male connector component comprising:
 a male connector body portion defining a male proximal end and a male distal end;
 a first lumen extending distally from said male distal end;
 a first fluid conduit defined by a first elongate bore extending from said male proximal end of said male connector body portion to said first lumen; and
 an elongate first latch arm extending distally from said male distal end, said first latch arm including an enlarged distal end defining a first latch catch and a lateral side surface extending between said first latch catch and said male distal end, said lateral side surface including a finger pad portion,
 wherein when the male and female connector components are coupled together by inserting said first latch arm into the first latch opening, said first latch catch snaps into engagement with the first latching shoulders at a position adjacent to the female proximal end, such that said first latch arm extends along a majority of a length between the female distal end and the female proximal end, and said finger pad portion of said first latch arm is accessible through the first access opening for a user to disengage said first latch catch from the first latching shoulder, wherein said first latch arm also includes a stiffening rib projecting inwardly and opposite said lateral side surface, said stiffening rib extending along at least a portion of said first latch arm between said enlarged distal end and said male distal end of said male connector body portion, and wherein said stiffening rib and said first latch arm collectively define an I-beam shaped cross section at said portion of said first latch arm.

26. The male connector component of claim 25, wherein the female connector component further includes a second receptacle and a second latch opening including an undercut formed in a portion of the female proximal end to define a second latching shoulder, and the male connector component further comprises:

a second lumen configured to be inserted in the second receptacle; and a second latch arm defining a second latch catch, with said first and second lumens located between said first and second latch arms, said second latch arm configured to be inserted in the second latch opening so that said second latch catch snaps into engagement with the second latching shoulder.

27. The male connector component of claim 26, further comprising:

an alignment feature configured to interact with another alignment feature on the female connector component to thereby prevent latching engagement of the male and female connector components unless said first lumen is aligned with the first receptacle and said second lumen is aligned with the second receptacle, wherein said alignment feature includes at least one of:

an elongate post or aperture positioned offset from a central axis through the male and female connector components;

a visual indicator in the form of coring or ribs formed in only one of said lateral side edges;

an asymmetrical male distal end face at said male distal end having first and second portions defining different curvatures; and an elliptical disc projection or elliptical disc aperture.

* * * * *